United States Patent
Hwang et al.

(10) Patent No.: US 10,149,817 B2
(45) Date of Patent: Dec. 11, 2018

(54) TOPICAL SKIN TREATMENT COMPOSITION COMPRISING DENDRANTHEMA INDICUM EXTRACT

(71) Applicant: AMOREPACIFIC CORPORATION, Seoul (KR)

(72) Inventors: Kyeong Hwan Hwang, Yongin-si (KR); Jun Seong Park, Yongin-si (KR); Hyang Tae Choi, Yongin-si (KR); Myeong Hun Yeom, Yongin-si (KR); Jun Cheol Cho, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 14/359,599

(22) PCT Filed: Nov. 6, 2012

(86) PCT No.: PCT/KR2012/009258
§ 371 (c)(1),
(2) Date: May 21, 2014

(87) PCT Pub. No.: WO2013/077569
PCT Pub. Date: May 30, 2013

(65) Prior Publication Data
US 2014/0295007 A1    Oct. 2, 2014

(30) Foreign Application Priority Data
Nov. 23, 2011 (KR) .......................... 10-2011-0122847

(51) Int. Cl.
*A61K 36/287* (2006.01)
*A61K 8/97* (2017.01)
*A61Q 19/00* (2006.01)
*A61Q 19/02* (2006.01)
*A61Q 19/08* (2006.01)

(52) U.S. Cl.
CPC .............. *A61K 8/97* (2013.01); *A61K 36/287* (2013.01); *A61Q 19/00* (2013.01); *A61Q 19/005* (2013.01); *A61Q 19/007* (2013.01); *A61Q 19/02* (2013.01); *A61Q 19/08* (2013.01); *A61K 2800/75* (2013.01)

(58) Field of Classification Search
CPC .............................. A61K 36/28; A61K 36/287
USPC .......................... 424/778, 779, 775, 774, 764
See application file for complete search history.

(56) References Cited

U.S. PATENT DOCUMENTS

2011/0052731 A1   3/2011   Park et al.
2011/0223265 A1   9/2011   Kim et al.

FOREIGN PATENT DOCUMENTS

| JP | 2005298481 A | * | 10/2005 |
| KR | 10-2004-0078956 A | | 9/2004 |
| KR | 20060108864 A | * | 10/2006 |
| KR | 10-2011-0001538 A | | 1/2011 |

OTHER PUBLICATIONS

Lin et al "Identification of the phenolic components of chrysanthemum flower (*Chrysanthemum morifolium Ramat*)", Food Chemistry 120 (2010) 319-326.*
International Searching Authority, International Search Report for PCT/KR2012/009258 dated Mar. 29, 2013.

* cited by examiner

*Primary Examiner* — Christopher R Tate
*Assistant Examiner* — Deborah A Davis
(74) *Attorney, Agent, or Firm* — Sughrue Mion, PLLC

(57) ABSTRACT

The present invention relates to a topical skin treatment composition comprising *Dendranthema indicum* extract and, more particularly, to a topical skin treatment composition containing *Dendranthema indicum* extract which is excellent for the anti-oxidation, anti-aging, whitening, and moisturizing of skin, and also does not cause skin irritation.

2 Claims, 2 Drawing Sheets

[FIG. 1]
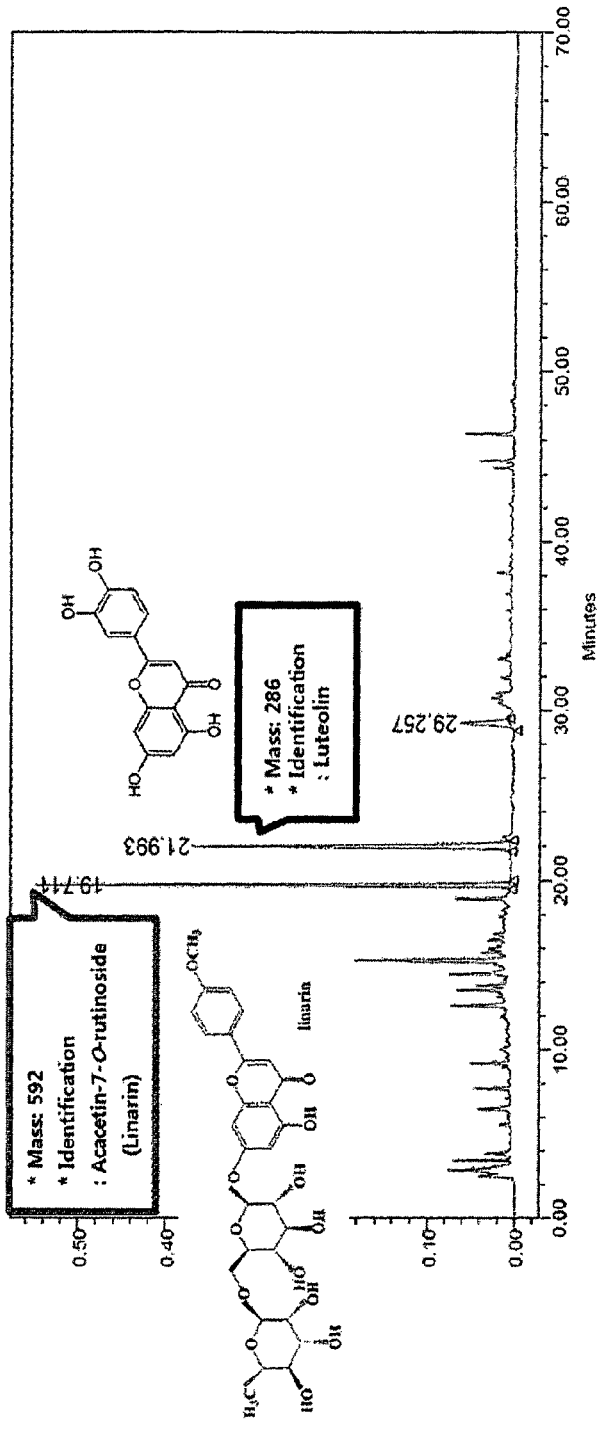

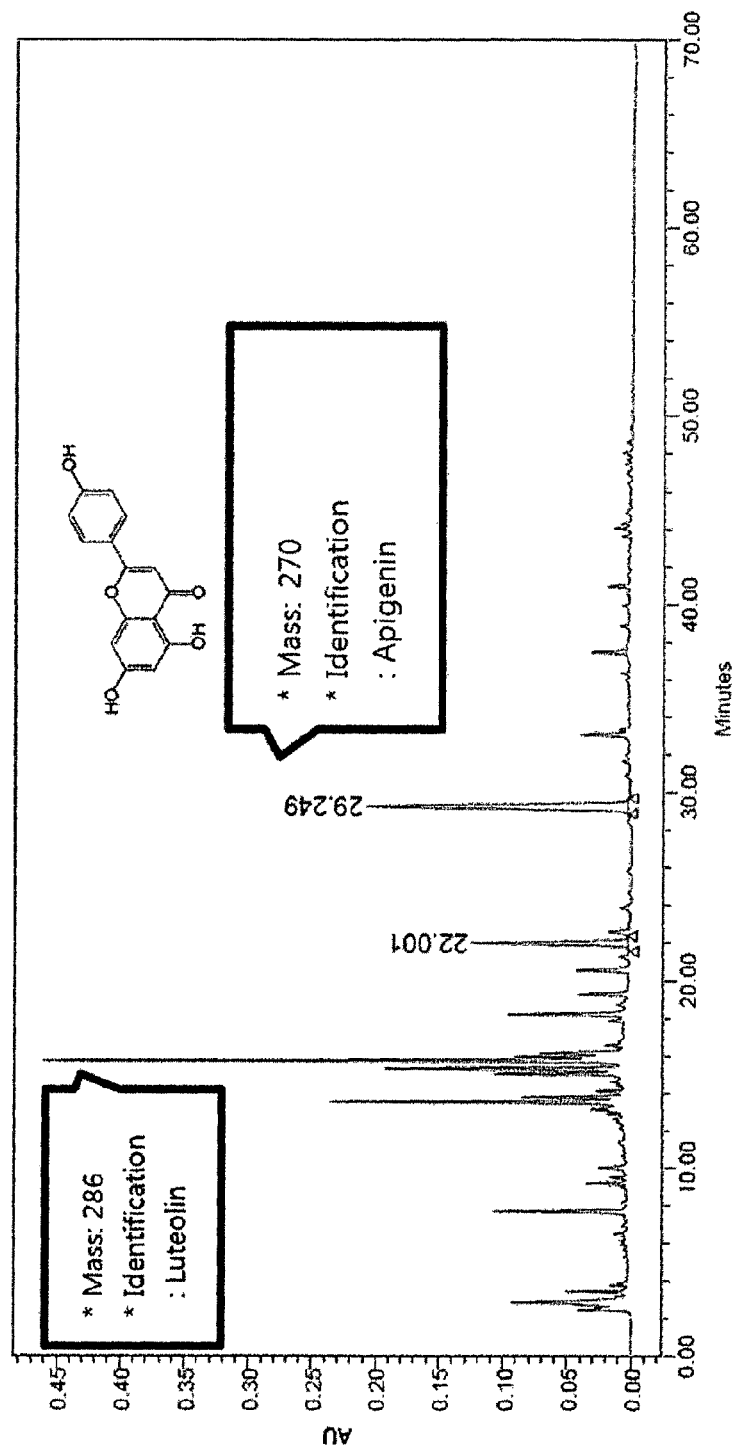
[FIG. 2]

TOPICAL SKIN TREATMENT COMPOSITION COMPRISING DENDRANTHEMA INDICUM EXTRACT

CROSS REFERENCE TO RELATED APPLICATIONS

This application is a National Stage of International Application No. PCT/KR2012/009258 filed Nov. 6, 2011, claiming priority based on Korean Patent Application No. 10-2011-0122847 filed Nov. 23, 2011, the contents of all of which are incorporated herein by reference in their entirety.

TECHNICAL FIELD

The present invention relates to a composition for external skin application, which contains an extract of *Chrysanthemum indicum* var. *albescens*, and more particularly to a composition for external skin application, which contains an extract of *Chrysanthemum indicum* var. *albescens*, which has excellent antioxidant, anti-aging, whitening and moisturizing effects on the skin without causing skin irritation.

BACKGROUND ART

Human skin undergoes changes with age due to a variety of internal and external factors. Specifically, with respect to the internal factors, the secretion of various hormones that regulate metabolism is reduced, the function of immunocytes and the activity of cells decline, and thus the biosynthesis of immune proteins and structural proteins that constitute a living body is reduced. With respect to the external factors, as the amount of ultraviolet rays reaching the earth's surface is increasing due to destruction of the ozone layer, and as environmental pollution becomes ever more serious, free radicals and reactive oxygen species increase. As a result, skin thickness decreases, wrinkles increase, skin elasticity decreases, the skin color becomes darker, skin troubles frequently arise, and age spots, freckles and dark spots also increase.

As aging progresses, the content and arrangement of collagen, elastin, hyaluronic acid and glycoprotein that constitute the skin are changed or decrease, and oxidative stress occurs due to free radicals and reactive oxygen species. Also, it is known that, as aging progresses or by the action of UV rays, in most cells of the skin, the biosynthesis of cyclooxygenase-2 (Cox-2) producing proinflammatory cytokines known to cause inflammation increases, the biosynthesis of matrix metalloproteinase (MMP) which degrades skin tissue increases due to these inflammatory factors, and the production of nitric oxide (NO) by inducible nitric oxide synthase (iNOS) increases. In other words, due to intrinsic aging that naturally progresses, the activity of cells is reduced, and the biosynthesis of substrates is reduced due to minute inflammation. In addition, due to external factors such as an increase in stress caused by various harmful pollutants and an increase in reactive oxygen species caused by the sunlight, degradation and denaturation are accelerated, and thus the skin matrix is broken and becomes thinner, while various symptoms of skin aging appear. For this reason, many studies on active ingredients that can prevent and ameliorate such aging phenomena are being conducted.

Meanwhile, it is known that reactive oxygen species which are produced by various physical, chemical and environmental factors, including enzyme systems, reduced metabolites, chemicals, pollutants and photochemical reactions, act as nonselective irreversible destroyers against lipids, proteins, sugar and DNA, which are the structural components of cells, thus causing various diseases, including cell aging and cancer. Also, various peroxides, including lipid peroxides which are produced as a result of lipid peroxidation by these reactive oxygen species, cause oxidative damage to cells, leading to various functional disorders, thus causing various diseases. Accordingly, antioxidants such as free radical scavengers or peroxide production inhibitors can be used as agents for inhibiting or treating aging and various diseases, which are caused by these oxides.

In the present invention, *Chrysanthemum indicum* var. *albescens* or *Chrysanthemum indicum* var. *albescens* Makino is a variety of *Chrysanthemum indicum* and has a botanical name of *Dendranthema indicum* f. *albescens*, *Dendranthema indicum* f. *albescens* (Makino) T. B. Lee, or the like. Generally, studies on *Chrysanthemum indicum* (yellow *Chrysanthemum*) have been conducted, but studies on *Chrysanthemum indicum* var. *albescens* (white *Chrysanthemum*) are insufficient, and the effect of *Chrysanthemum indicum* var. *albescens* on the skin has not yet been reported.

DISCLOSURE

Technical Problem

Accordingly, the present inventors have found that, when an extract of *Chrysanthemum indicum* var. *albescens* is used as a composition for external skin application, it exhibits excellent antioxidant, anti-aging, whitening and moisturizing effects on the skin without causing skin irritation and has excellent effects compared to conventional *Chrysanthemum indicum* extracts, thereby completing the present invention.

Therefore, it is an object of the present invention to provide a composition for external skin application, which an extract of *Chrysanthemum indicum* var. *albescens*, which has excellent antioxidant, anti-aging, whitening and moisturizing effects on the skin.

Technical Solution

In order to accomplish the above object, the present invention provides an external skin application composition for anti-oxidation, which contains an extract of *Chrysanthemum indicum* var. *albescens* as an active ingredient.

The present invention also provides an external skin application composition for anti-aging, which contains an extract of *Chrysanthemum indicum* var. *albescens* as an active ingredient.

The present invention also provides an external skin application composition for improving skin elasticity, which contains an extract of *Chrysanthemum indicum* var. *albescens* as an active ingredient.

The present invention also provides an external skin application composition for reducing skin wrinkles, which contains an extract of *Chrysanthemum indicum* var. *albescens* as an active ingredient.

The present invention also provides an external skin application composition for skin whitening, which contains an extract of *Chrysanthemum indicum* var. *albescens* as an active ingredient.

The present invention also provides an external skin application composition for moisturization, which contains an extract of *Chrysanthemum indicum* var. *albescens* as an active ingredient.

Advantageous Effects

The present invention can provide excellent antioxidant, anti-aging, whitening and moisturizing effects on the skin without causing skin irritation by containing an extract of *Chrysanthemum indicum* var. *albescens*.

DESCRIPTION OF DRAWINGS

FIG. 1 is a graphic diagram showing the results of analyzing the components of an extract of *Chrysanthemum indicum* var. *albescens* (white *Chrysanthemum*) by HPLC.

FIG. 2 is a graphic diagram showing the results of analyzing the components of an extract of *Chrysanthemum indicum* (yellow *Chrysanthemum*) by HPLC.

BEST MODE

The composition for external skin application according to the present invention contains an extract of *Chrysanthemum indicum* var. *albescens* or *Chrysanthemum indicum* var. *albescens* Makino as an active ingredient.

The extract of *Chrysanthemum indicum* var. *albescens* according to the present invention can be obtained by a method known in the art. For example, the extract of the present invention can be prepared by washing *Chrysanthemum indicum* var. *albescens* with purified water, drying the washed plant with sunlight or hot air, finely powdering the dried plant, and extracting the powder with an extraction solvent. The extraction solvent that is used in the present invention may be selected from among organic solvents, including ethanol, methanol, butanol, ether, ethyl acetate and chloroform, and mixed solvents of these organic solvents and water. In view of the safety of the raw material, water or 30-70% ethanol is preferably used in the present invention. The extract obtained using the solvent as described above may be extracted under reflux, filtered, and concentrated under reduced pressure at a temperature of 40~45° C., thereby obtaining a dry extract of *Chrysanthemum indicum* var. *albescens*.

The composition of the present invention preferably contains the extract of *Chrysanthemum indicum* var. *albescens* in an amount of 0.001-10 wt % based on the total weight of the composition. If the content of the extract of *Chrysanthemum indicum* var. *albescens* in the composition is less than 0.001 wt %, the efficacy and effect of the extract will be insignificant, and if the content of the extract is more than 10 wt %, it will cause problems in terms of skin safety and formulation.

The composition of the present invention may be used as an external skin application composition for anti-oxidation, which shows an excellent antioxidant effect by scavenging or inhibiting free radicals.

The composition of the present invention may be used as a composition may be used an external skin application composition for anti-aging, which has excellent effects of improving skin elasticity and reducing wrinkles.

The composition of the present invention may be used as a composition may be used an external skin application composition for moisturization, which can enhance skin barrier function and induce the differentiation of skin keratinocytes.

The composition of the present invention may be used as a composition may be used an external skin application composition for skin whitening, which exhibits excellent whitening effects of inhibiting tyrosinase activity and melanin production.

The composition according to the present invention contains a cosmetically and skin-scientifically acceptable medium or base. The composition may be formulated as a preparation for local application. Examples of formulations for local application include a solution, a gel, a solid, a paste anhydride, an oil-in-water emulsion, a suspension, a microemulsion, microcapsules, microgranules, ionic (liposome) and non-ionic vesicles, cream, skin toner, lotion, powder, ointment, spray, or conceal stick. Also, the composition according to the present invention can be formulated as a foamed composition or an aerosol composition further containing a compressed propellant. In addition, the composition of the present invention can be formulated according to a conventional method known in the art.

Further, the composition according to the present invention may contain additives which are conventionally used in the cosmetic field or the skin science field, for example, a fatty substance, an organic solvent, a solubilizing agent, a thickener, a gelling agent, a softener, an antioxidant, a suspending agent, a stabilizer, a foaming agent, an aromatic, a surfactant, water, an ionic or non-ionic emulsifying agent, a filler, a sequestering agent, a chelating agent, a preservative, vitamins, a blocker, a moisturizing agent, essential oil, a dye, a pigment, a hydrophilic or hydrophobic activator, a lipid vesicle, or other components which are generally used in cosmetics. These additives are contained in amounts which are generally used in the cosmetic field or the skin science field.

Further, the composition of the present invention may contain a skin absorption-promoting material in order to increase the effects of improving skin conditions.

In addition, the composition of the present invention may contain, in addition to the extract of *Chrysanthemum indicum* var. *albescens*, other components capable of increasing the skin protective effect, within a range that does not impair the antioxidant, anti-aging, moisturizing and whitening effects of the present invention.

MODE FOR INVENTION

Hereinafter, the construction and effect of the present invention will be described in further detail with reference to test examples and formulation examples. It is to be understood, however, that these test examples and formulation examples are for illustrative purposes and are not intended to limit the scope of the present invention.

Preparation Example 1: Preparation of Extract of *Chrysanthemum indicum* Var. *Albescens*

*Chrysanthemum indicum* var. *albescens* harvested in a fresh state was washed with purified water, dried by sunlight, and then finely powdered. To 100 g of the powder was added 1000 ml of 70% ethanol, extracted under reflux, filtered, and concentrated under reduced pressure at a temperature of 40~45° C., thereby obtaining 17.1 g of an extract of *Chrysanthemum indicum* var. *albescens*.

Comparative Preparation Example 1: Preparation of Extract of *Chrysanthemum indicum* (Yellow *Chrysanthemum*)

An extract was prepared in the same manner as described in Preparation Example 1, except that *Chrysanthemum indicum* (yellow *chrysanthemum*) was used in place of *Chrysanthemum indicum* var. *albescens*.

Test Example 1: Analysis of Components of *Chrysanthemum Indicum* Extract and *Chrysanthemum indicum* Var. *Albescens* Extract The components of 10 mg/me of each of the *Chrysanthemum indicum* var. *albescens* extract prepared in Preparation Example 1 and the *Chrysanthemum indicum* extract prepared in Comparative Preparation Example 1 were analyzed by HPLC, and the results of the analysis are shown in Table 1 below and FIGS. 1 and 2.

TABLE 1

| Unit (mg/g) | Linarin (acacetin-7-O-rutinoside) | Luteolin | Apigenin |
|---|---|---|---|
| Comparative Preparation Example 1 | — | 2.5 | 5.7 |
| Preparation Example 1 | 14.9 | 6.4 | 1.6 |

As can be seen in Table 1 above, the *Chrysanthemum indicum* extract does not contain linarin known as an antioxidant active substance, whereas the *Chrysanthemum indicum* var. *albescens* extract contains a large amount of linarin.

Test Example 2: Test for Antioxidant Effect (DPPH Test)

In order to examine the antioxidant effect of the *Chrysanthemum indicum* var. *albescens* extract prepared in Preparation Example 1 and the *Chrysanthemum indicum* extract prepared in Comparative Preparation Example 1, the antioxidant effect was measured based on the change in absorbance resulting from reduction of the organic radical 1,1-diphenyl-2-picrylhydrazyl (DPPH) (the antioxidant is oxidized). Specifically, the decrease in absorbance resulting from the inhibition of DPPH oxidation caused by each of the *Chrysanthemum indicum* var. *albescens* extract prepared in Preparation Example 1 and the *Chrysanthemum indicum* extract prepared in Comparative Preparation Example 1 was measured, and the concentration at which the absorbance decreased to 50% of control was determined as the effective antioxidant concentration.

10 µl of each of the *Chrysanthemum indicum* var. *albescens* extract prepared in Preparation Example 1, the *Chrysanthemum indicum* extract prepared in Comparative Preparation Example 1, and a positive control, was added to 190 µl of 100 µM DPPH solution (in ethanol) to make reaction solutions. Each of the reaction solutions was allowed to react at 37° C. for 30 minutes, and the absorbance at 540 nm was measured. The positive control used was the synthetic antioxidant Trolox which is widely used. The results of DPPH analysis of each test sample are shown in Table 2 below, and $IC_{50}$ in Table 2 means the sample concentration at which the absorbance was decreased by 50% due to the sample added.

TABLE 2

| Test sample | $IC_{50}$ (ppm) |
|---|---|
| Trolox | 43 |
| *Chrysanthemum indicum* var. *albescens* extract (Preparation Example 1) | 48 |
| *Chrysanthemum indicum* extract (Comparative Preparation Example 1) | 107 |

As can be seen in Table 2 above, the antioxidant effect of the *Chrysanthemum indicum* var. *albescens* extract of Preparation Example 1 was similar to that of the synthetic antioxidant Trolox used as the positive control and was at least two times higher than that of the *Chrysanthemum indicum* extract of Comparative Preparation Example 1. This suggests that the *Chrysanthemum indicum* var. *albescens* extract according to the present invention has an excellent antioxidant effect.

Test Example 3: Anti-Aging Effect—Effect on Inhibition of Collagenase Expression The collagenase expression inhibitory activities of the *Chrysanthemum indicum* var. *albescens* extract prepared in Preparation Example 1 and the *Chrysanthemum indicum* extract prepared in Comparative Preparation Example 1 were measured comparatively with those of tocopherol and EGCG. Tocopherol and EGCG are antioxidant substances known to function to regenerate the epidermal cells of the skin to prevent the aging of the skin.

In the test, human fibroblasts were added to a 96-well microtiter plate containing 2.5% FBS-containing DMEM (Dulbecco's Modified Eagle's Media) medium at a density of 5,000 cells/well and were cultured to a confluence of about 90%. Next, the cells were cultured in serum-free medium for 24 hours, and then treated with 50 ppm of each of the *Chrysanthemum indicum* var. *albescens* extract of Preparation Example 1 and the *Chrysanthemum indicum* extract of Comparative Preparation Example 1 in serum-free DMEM medium or $10^{-4}$ M of each of tocopherol and EGCG for 24 hours, after which the cell cultures were harvested.

The production of collagenase in the harvested cell cultures was measured using a commercially available collagenase measuring device (Amersham Pharmacia, USA). Specifically, the harvested cells were added to a 96-well plate having primary collagenase antibody applied uniformly thereto and were subjected to an antigen-antibody reaction in a constant-temperature bath for 3 hours After 3 hours, chromophore-conjugated secondary collagen antibody was added to the 96-well plate and allowed to react for 15 minutes. After 15 minutes, a substance inducing color development was added to the 96-well plate, and color development was induced at room temperature for 15 minutes. When 1M sulfuric acid was added to the 96-well plate to stop the reaction (color development), the reaction solution had a yellow color, and the intensity of the yellow color varied depending on the degree of progression of the reaction.

The absorbance of the 96-well plate having a yellow color was measured at 405 nm using a spectrophotometer, and the degree of synthesis of collagenase was calculated using the following Equation 1. Herein, the absorbance of the cell culture broth harvested from the group not treated with the test material was used as a control. That is, the expression level of collagenase in the untreated group was set as 100, and the expression level of collagenase in the group treated with the test material was calculated relative to the untreated group. The calculation results are shown in Table 3 below.

Collagenase expression level(%)=absorbance of group treated with test material/absorbance of control group×100       Equation 1

TABLE 3

| Test material | Collagenase expression level (%) |
|---|---|
| Untreated group | 100 |
| Tocopherol | 76 |
| EGCG | 69 |
| *Chrysanthemum indicum* var. *albescens* extract (Preparation Example 1) | 64 |
| *Chrysanthemum indicum* extract (Comparative Preparation Example 1) | 81 |

As the expression level of collagenase becomes lower, the ability of the test material to inhibit collagenase expression is higher, the degradation of collagen in the skin is reduced so that a decrease in skin elasticity is inhibited and the formation of wrinkles is reduced. As can be seen in Table 3 above, the *Chrysanthemum indicum* var. *albescens* extract of the present invention effectively inhibited the expression of collagenase in vitro and had excellent inhibitory effects on collagenase expression compared to tocopherol and EGCG.

Particularly, the *Chrysanthemum indicum* var. *albescens* extract more effectively inhibited the expression of collagenase compared to the *Chrysanthemum indicum* extract, suggesting that it exhibits excellent anti-aging effects by reducing the degradation of collagen in the skin to improve skin elasticity and reduce skin wrinkles.

Test Example 4: Whitening Effect—Test for Melanin Production Inhibitory Effect Using Mouse Melanocytes The melanin production inhibitory activities of the *Chrysanthemum indicum* var. *albescens* extract prepared in Preparation Example 1 and the *Chrysanthemum indicum* extract prepared in Comparative Preparation Example 1 were measured comparatively with those of the known whitening substance hydroquinone.

C57BL/6 mouse melanocytes (Mel-Ab cells) (Dooley, T. P. et al, Skin pharmacol, 7, pp 188-200) were cultured in DMEM, containing 10% fetal bovine serum, 100 nM 12-O-tetradecanoylphorbol-13-acetate and 1 nM cholera toxin, under the conditions of 37° C. and 5% $CO_2$. The cultured Mel-Ab cells were detached with 0.25% trypsin-EDTA and cultured in a 24-well plate at a concentration of 10 cells/well. Then, during three consecutive days from 2 days of culture, each of the test materials was added thereto and cultured. As the test materials, 25 ppm of each of the *Chrysanthemum indicum* var. *albescens* extract of Preparation Example 1, the *Chrysanthemum indicum* extract of Comparative Preparation Example 1, and hydroquinone were used. Herein, the hydroquinone was used as a positive control. Then, the media were removed, and the cells were washed with PBS and lysed with 1N sodium hydroxide. The lysed cells were measured for absorbance at 400 nm, and based on the measured absorbance, the percent inhibition of melanin production was calculated according to the following equation 2. The results of the calculation are shown in Table 4 (Dooley's method).

$$\text{Percent inhibition of melanin production}=100-(\text{absorbance of test material/absorbance of control}\times 100) \quad \text{Equation 2}$$

TABLE 4

| Test material | Inhibition (%) of melanin production |
|---|---|
| Untreated group | 100 |
| Hydroquinone (positive control) | 48.2 |
| *Chrysanthemum indicum* var. *albescens* extract (Preparation Example 1) | 54.9 |
| *Chrysanthemum indicum* extract (Comparative Preparation Example 1) | 29.4 |

As can be seen in Table 4 above, the *Chrysanthemum indicum* var. *albescens* extract of the present invention showed melanin production inhibitory activity similar to that of the known whitening substance hydroquinone and more effectively inhibited melanin production compared to the *Chrysanthemum indicum* extract, suggesting that it has an excellent whitening effect.

Test Example 5: Irritation Test

In order to compare the sensory feeling of the *Chrysanthemum indicum* var. *albescens* extract of the present invention with that of the known whitening substance kojic acid, 15 panels sensitive to irritation, such as stinging, burning, etc., were subjected to a test for determining irritation, such as stinging, burning, etc.

Each test panel was allowed to apply 0.5 mL of each of kojic acid (available from YM Chemical Co.) and the *Chrysanthemum indicum* var. *albescens* extract to his/her skin randomly at the left side or right side, and then evaluate the test sample by grading from 0 to 3.0 at an interval of 0.1. The results are shown in Table 5 below.

Criteria for Evaluation
0-0.4: no irritation;
0.5-1.0: slight irritation;
1.1-2.0: mild irritation;
2.1-3.0: severe irritation.

TABLE 5

| | Kojic acid | *Chrysanthemum indicum* var. *albescens* extract (Preparation Example 1) |
|---|---|---|
| Stinging | 0.91 | 0.23 |
| Burning | 0.43 | 0.14 |
| Average | 0.67 | 0.19 |

As can be seen in Table 5 above, kojic acid caused slight stinging and burning and a perceptible degree of irritation. On the contrary, the *Chrysanthemum indicum* var. *albescens* extract of the present invention caused little or no irritation with respect to stinging and burning. This suggests that the *Chrysanthemum indicum* var. *albescens* extract of the present invention causes no irritation, and thus can give a good sensory feeling, compared to kojic acid.

Test Example 6: Skin Moisturization Test—Test for Induction of Differentiation of Human Keratinocytes In order to examine the skin barrier function and skin moisturizing activity of each of the *Chrysanthemum indicum* var. *albescens* extract prepared in Preparation Example 1 and the *Chrysanthemum indicum* extract prepared in Comparative Preparation Example 1, the following test was performed using absorbance.

Human neonatal epidermal keratinocytes (HEK; Lonza, NHEK-Neo-Neonatal Normal Human Epidermal Keratinocytes, Pooled) were dispensed in medium (KBM-gold, Lonza) in a 6-well plate at a density of $5 \times 10^4$ cells per well and cultured for 24 hours under the conditions of 37° C. and 5% $CO_2$. Next, each of the *Chrysanthemum indicum* var. *albescens* extract and the *Chrysanthemum indicum* extract was added to the cell culture at concentrations of 50 ppm and 100 ppm, and the cells were cultured to a confluence of 80-90% for 5 days. The cells were harvested and washed with PBS (phosphate buffered saline), and then 1 ml of 10 mM Tris-HCl buffer (pH 7.4) containing 2% SDS (sodium dodecyl sulfate) and 20 mM DTT (dithiothreitol) was added to the cells, followed by sonication for 3 minutes and boiling for 10 minutes. The resulting solution was centrifuged at 1200 rpm for 30 minutes, and the precipitate was suspended in 1 ml of PBS. The absorbance of the suspension at 340 nm was measured.

Meanwhile, a portion of the solution after the sonication was taken and the protein content thereof was measured and used as a standard for evaluating the differentiation of the cells. A low-calcium (0.03 mM) group and a high-calcium (1.2 mM) group were used as negative/positive control groups, respectively. Each of the test materials was added at low calcium concentration, and the amount of CE (cornified envelope) produced during keratinocyte differentiation was measured to determine the cell differentiation-promoting effect of the test material. The results of the measurement are shown in Table 6 below.

TABLE 6

| Test material | Concentration | Keratinocyte differentiation (%) |
|---|---|---|
| Control | Low-calcium group (0.03 mM) | 100 |
|  | High-calcium group (1.2 mM) | 208 |
| *Chrysanthemum indicum* var. *albescens* extract (Preparation Example 1) | 50 ppm | 128 |
|  | 100 ppm | 153 |

TABLE 6-continued

| Test material | Concentration | Keratinocyte differentiation (%) |
|---|---|---|
| *Chrysanthemum indicum* extract (Comparative Preparation Example 1) | 50 ppm | 109 |
|  | 100 ppm | 124 |

As can be seen in Table 6 above, the *Chrysanthemum indicum* var. *albescens* extract of the present invention promoted the differentiation of keratinocytes. Particularly, the *Chrysanthemum indicum* var. *albescens* extract more effectively promoted the differentiation of keratinocytes, suggesting that it enhances skin barrier function and skin moisturization.

INDUSTRIAL APPLICABILITY

As described above, the present invention provides the composition that has excellent antioxidant, anti-aging, whitening and moisturizing effects on the skin without causing skin irritation.

The invention claimed is:

1. A method for improving skin condition of a subject, comprising applying a composition comprising an extract of a plant as an active ingredient and a cosmetically acceptable additive to skin of the subject,
   wherein the plant consists of *Chrysanthemum indicum* var. *albescens*;
   wherein the improvement of skin condition is selected from the group consisting of improved moisturization and improved brightness; and
   wherein the composition is selected from the group consisting of a solution, a gel, a solid, a paste anhydride, an oil-in-water emulsion, a suspension, a microemulsion, microcapsules, microgranules, liposome, non-ionic vesicles, cream, skin toner, lotion, powder, ointment, spray, conceal stick, foamed composition, and an aerosol composition,
   wherein the extract of plant is obtained by extracting the plant with 30 to 70% ethanol.

2. The method of claim 1, wherein the extract of plant is contained in an amount of 0.001-10 wt % based on the total weight of the composition.

* * * * *